(12) United States Patent
Adekore

(10) Patent No.: US 10,935,539 B1
(45) Date of Patent: Mar. 2, 2021

(54) EMBEDDED EXCRETA ANALYSIS DEVICE AND RELATED METHODS

(71) Applicant: Bunmi T. Adekore, Medford, MA (US)

(72) Inventor: Bunmi T. Adekore, Medford, MA (US)

( * ) Notice: Subject to any disclaimer, the term of this patent is extended or adjusted under 35 U.S.C. 154(b) by 0 days.

(21) Appl. No.: 15/725,233

(22) Filed: Oct. 4, 2017

Related U.S. Application Data

(60) Provisional application No. 62/405,880, filed on Oct. 8, 2016.

(51) Int. Cl.

| | |
|---|---|
| *G01N 33/48* | (2006.01) |
| *G01N 33/487* | (2006.01) |
| *G01N 21/31* | (2006.01) |
| *G01N 21/65* | (2006.01) |
| *G01N 21/47* | (2006.01) |
| *G01N 33/53* | (2006.01) |
| *G01N 21/64* | (2006.01) |
| *A61B 10/00* | (2006.01) |
| *G01N 33/483* | (2006.01) |
| *G01N 33/493* | (2006.01) |

(52) U.S. Cl.
CPC ..... *G01N 33/4875* (2013.01); *A61B 10/0038* (2013.01); *G01N 21/3103* (2013.01); *G01N 21/47* (2013.01); *G01N 21/64* (2013.01); *G01N 21/65* (2013.01); *G01N 33/5302* (2013.01); *G01N 33/48* (2013.01); *G01N 33/4833* (2013.01); *G01N 33/493* (2013.01)

(58) Field of Classification Search
CPC ............................ G01N 33/48; A61B 10/0038
See application file for complete search history.

(56) References Cited

U.S. PATENT DOCUMENTS

| | | | |
|---|---|---|---|
| 4,170,798 A | * 10/1979 | Krumdieck | G01N 1/04 |
| | | | 141/130 |
| 5,073,500 A | 12/1991 | Saito | |
| | (Continued) | | |

OTHER PUBLICATIONS

Langhorst J, Elsenbruch S, Mueller T, Rufer A, Spahn G, Michalsen A, Dobos GJ; Comparison of 4 neutrophil-derived proteins in feces as indicators of disease activity in ulcerative-colitis; Inflamm. Bowel. Dis. 2005; 11:1085-91. [PinMed:16306771].

(Continued)

*Primary Examiner* — Jonathan M Hurst

(57) ABSTRACT

In an embodiment, a system for analyzing excreta, wherein the system is configured to collect and analyze at least a portion of an excreta, wherein at least a portion of the system is configured to be embedded in an excreta disposal unit, and wherein the system comprises at least one electronic device. In a further embodiment, an analysis system for analyzing excreta, comprises a first portion configured to be connected to an excreta disposal unit and configured to collect at least a portion of an excreta, and a second portion configured to homogenize the at least a portion of the excreta collected by the first portion. In a further embodiment, an analysis system for analyzing excreta comprises a first portion of configured to be connected to an excreta disposal unit and configured to collect at least a portion of an excreta, and wherein the analysis system is configured to detect analyte from multiple users.

20 Claims, 11 Drawing Sheets

(56) References Cited

U.S. PATENT DOCUMENTS

| | | | |
|---|---|---|---|
| 6,093,422 A * | 7/2000 | Denkewicz, Jr. | A01N 59/16 424/618 |
| 8,194,514 B2 | 6/2012 | Yu | |
| 9,913,626 B1 * | 3/2018 | Hall | A61B 10/0038 |
| 2016/0000378 A1 * | 1/2016 | Hall | A61B 5/0075 702/19 |

OTHER PUBLICATIONS

James D. Lewis, MD, MSCE; The Utility of Biomarkers in Diagnosis and Therapy of Inflammatory Bowel Disease; Gastroenterology. May 2011;140 (6): 1817-1826.e2. dos: 10.1053/j.gastro.2010.11.058.

Vermeire S, Van Assche G, Rutgeerts P.; Laboratory markers in IBD: useful, magic or unnecessary toys. Gut. 2006, 55:436-31 [PubMed: 16474114].

Kane SV, Sandborn WJ, Rufo PA, Zholudev A, Boone J, Lyerly D, Camilleri M, Hanauer SB.; Fecal Lactoferrin is a sensitive and specific marker in identifying intestinal inflammation. Am J. Gastroenterol. 2003, 98:309-14 [PubMed:12818275].

Roseth AG, Fagerhol MK, Aadland E, Schjonsby H., Assessment of the neutrophil dominating protein calproctectin in feces. A methodology study. Scand. J. Gastroenterol. 1992; 27: 793-8. [PubMed: 1411288].

Kolho KL, Turner D, Veereman-Wauters G, et al, Rapid test for fecal calprotectin levels in child with Crohn's disease. J. Pediatr. Gastroenterol Nutr. 2012; 55: 436-439.

Reese GE, Constantinides VA, Simillis C, Darzi AW, Orchard TR, Fazio VW, Tekkis PP. Diagnostic precision of anti-*Saccharomyces cerevisiae* antibodies and perinuclear antineutrophil cytoplasmic antibodys in inflammatory bowel disease. Am. J.Gastroenterol. 2006; 101: 2410-22 [PubMed: 16952282].

Bunn SK, Bisset WM, Main MJ et al., Fecal calprotectin as a measure of disease activity in childhood inflammatory bowel disease. J. Pediatr. Gastroenterol. Nutr. 2001; 32:171-177.

Masodi I, Kochhar R, Dutta U, Vaishnavi C, Prasad KK, Vaiphei K, Kaur S, Singh K, Fecal lactoferrin, myeloperoxidase and serum C-reactive are effective biomarkers in the assessment of disease activity and severity in patients with idiopathic ulcerative colitis. J.Gastroenterol Hepatol. 2009; 24:1768-74. [PubMed:20136960].

Poullis AP, Zar S, Sundaram KK, Moodie SJ, Sisley P, Theodors A, Mental MA.; A new, highly sensitive assay for C-reactive protein can aid the differentiation of inflammatory bowel disorders from constipation- and diarrhea-predominant functional bowel disorders. Eur. J. Gastroenterol. Hepato. 2002; 14:409-12 [PubMed:11943955].

G. Van Asshce, Fecal Biomarkers for the Diagnosis and Management of Inflammatory Bowel Disease; Gastroenteroloy & hepatology; 7, No. 6 (2011) 396.

Carroccio, Antonio et al. "Diagnostic accuracy of fecal calprotectin assay in distinguishing organic causes of chronic diarrhea from irritable bowel syndrome: a prospective study in adults and children." Clinical chemistry 49.6 (2003): 861-867.

Gisbert JP, McNicholl AG. Questions and answers on the role of faecal cal-protectin as a biological marker in inflammatory bowel disease. Dig Liver Dis. 2009;41:56-66.

Von Roon AC, Karamountzos L, Purkayastha S, Reese GE, Darzi AW, Teare JP, Paraskeva P, Tekkis PP. Diagnostic precision of fecal calprotectin for inflammatory bowel disease and colorectal malignancy. Am. J. Gastroenterol. 2007; 102:803-13. [PubMed:17324124].

Labaere Delphine et al. "Comparison of six different calprotectin assays for the assessment of inflammatory bowel disease." United European Gastroenterology Journal 2.1 (2014): 30-37.

Van Rheenen, Patrick F., Els Van de Vijver, and Vaclav Fidler. "Faecal calprotectin for screening of patients with suspected inflammatory bowel disease: diagnostic meta-analysis." Bmj 341 (2010): c3369.

De Jong NS, Leach ST, Day AS. Fecal S100A12: a novel noninvasive marker in children with Crohn's disease. Inflamm Bowel Dis. 2006; 12:566-72. [PubMed: 16804393].

Sidler, Marc A., Steven T. Leach, and Andrew S. Day. "Fecal S100A12 and fecal calprotectin as noninvasive markers for inflammatory bowel disease in children." Inflammatory bowel diseases 14.3 (2008): 359-366.

Kaiser T., Langhorst J, Wittkowski H, Becker K, Friedrich AW, Rueffer A, Dobos GJ, Roth J, Foell D. Faecal S100A12 as a noninvasive marker distinguishing inflammatory bowel disease from irritable bowel syndrome. Gut. 2007; 56:1706-13. [PubMed:17675327].

Manolakis AC, Kapsoritakis AN, Georgoulias P, Tzavara C, Valotassiou V, Kapsoritaki A, Potamianos SP. Moderate performance of serum S100A12, in distinguishing inflammatory bowel disease from irritable bowel syndrome. BMC Gastroenterol. 2010; 10:118. [PubMed: 20946669].

* cited by examiner

EMBEDDED EXCRETA ANALYSIS DEVICE AND RELATED METHODS

CROSS-REFERENCE TO RELATED APPLICATIONS

The present application claims priority to U.S. Provisional Patent Application No. 62/405,880, filed Oct. 8, 2016, entitled "Embedded Excreta Analysis Device" the entire content of which is incorporated by reference herein.

BACKGROUND OF THE INVENTION

1. The Field of the Invention

The disclosed apparatus and method relate generally to analysis of excreta.

2. Background and Relevant Art

Fecal biomarkers (Langhorst, J, Eisenbruch S, Mueller T, Rufer A, Spahn G, Michalsen A, Dobos G J; Comparison of 4 neutrophil-derived proteins in feces as indicators of disease activity in ulcerative-colitis; Inflamm. Bowel. Dis. 2005; 11:1085-91. [PinMed:16306771]; James D. Lewis, MD, MSCE; The Utility of Biomarkers in Diagnosis and Therapy of Inflammatory Bowel Disease; Gastroenterology. 2011 May; 140 (6): 1817-1826.e2. dos: 10.1053/j.gastro.2010.11.058) for example calprotectin (Vermeire S, Van Assche G, Rutgeerts P.; Laboratory markers in IBD: useful, magic or unnecessary toys. Gut. 2006, 55:436-31 [PubMed: 16474114]) and lactoferrin (Kane S V, Sandborn W J, Rufo P A, Zholudev A, Boone J, Lyerly D, Camilleri M, Hanauer S B.; Fecal Lactoferrin is a sensitive and specific marker in identifying intestinal inflammation. Am J. Gastroenterol. 2003, 98:309-14 [PubMed:1281 8275]) which are secreted by inflammatory cells, neutrophils, can be effective instruments for the early diagnosis and management of a variety of acute and terminal diseases including cancer, crohn's disease, ulcerative colitis, inflammatory bowel disease (IBD) as well as other colonic, ileal and/or mucosal disease. While calprotectin which is 36 kDa calcium- and zinc-binding protein that represents 60% of cytosolic proteins in granulocytes, is stable in feces at room temperature for up to one week (Roseth A G, Fagerhol M K, Aadland E, Schjonsby H., Assessment of the neutrophil dominating protein calproctectin in feces. A methodology study. Scand. J. Gastroenterol. 1992; 27: 793-8. [PubMed: 1411288]); Lactoferrin2 is an iron-binding protein found in neutrophil granules and serum and is secreted by mucosal membranes.

In addition to the highly desirable non-invasive attributes associated with utility of fecal biomarker which is of tremendous value where there is need to eliminate full endoscopy or colonoscopy evaluation or reduce the frequency of endoscopic intervention, for instance in pediatric patients (Kolho K L, Turner D, Veereman-Wauters G, et al, Rapid test for fecal calprotectin levels in child with Crohn's disease. J. Pediatr. Gastroenterol Nutr. 2012; 55: 436-439; Reese G E, Constantinides V A, Simillis C, Darzi A W, Orchard T R, Fazio V W, Tekkis P P. Diagnostic precision of anti-*Saccharomyces cerevisiae* antibodies and perinuclear antineutrophil cytoplasmic antibodys in inflammatory bowel disease. Am. J. Gastroenterol. 2006; 101: 2410-22 [PubMed: 16952282]; Bunn S K, Bisset W M, Main M J et al., Fecal calprotectin as a measure of disease activity in childhood inflammatory bowel disease. J. Pediatr. Gastroenterol. Nutr. 2001; 32:171-177); an added advantage of fecal biomarkers when compared with serologic biomarkers such as C-reactive protein (CRP) (Masodi I, Kochhar R, Dutta U, Vaishnavi C, Prasad K K, Vaiphei K, Kaur S, Singh K, Fecal lactoferrin, myeloperoxidase and serum C-reactive are effective biomarkers in the assessment of disease activity and severity in patients with idiopathic ulcerative colitis. J. Castroenterol Hepatol. 2009; 24:1768-74. [PubMed: 20136960]; Polls A P, Zar S, Sundaram K K, Moodie S J, Sisley P, Theodors A, Mental M A.; A new, highly sensitive assay for C-reactive protein can aid the differentiation of inflammatory bowel disorders from constipation- and diarrhea-predominant functional bowel disorders. Eur. J. Gastroenterol. Hepato. 2002; 14:409-12 [PubMed:11943955]) is its specificity i.e., fecal biomarker testing measure protein originating from the intestinal mucosa and reflect purely intestinal inflammation.

However, the specificity of fecal biomarkers is limited to intestinal inflammation or intestinal lesions and which specificity is significantly lowered in the evaluation of IBD. For example patients undergoing nonsteriodal anti-inflammatory drugs (NSAIDs) (G Van Asshce, Fecal Biomarkers for the Diagnosis and Management of Inflammatory Bowel Disease; Gastroenterology & hepatology; 7, no. 6 (2011) 396; Carroccio, Antonio, et al. "Diagnostic accuracy of fecal calprotectin assay in distinguishing organic causes of chronic diarrhea from irritable bowel syndrome: a prospective study in adults and children." Clinical chemistry 49.6 (2003): 861-867) there is an increase in fecal inflammatory markers including calprotectin or lactoferrin. As such, a negative fecal biomarker result is predictive that no lesions exists in the bowel however a positive fecal biomarker test is less indicative or specific. The positive fecal biomarker result may indicate the presence of a lesion in bowel but it is unclear it is associated with IBD. Therefore, fecal biomarker testing has a very high negative predictive value but its positive predictive value is lower.

In addressing whether fecal biomarkers can be used to select patients that warrant endoscopic or radiologic evaluation, whereas there is noticeable statistically spread in performance data reported for calprotectin and lactoferrin tests, Gisbert et al (Gisbert J P, McNicholl A G. Questions and answers on the role of faecal cal-protectin as a biological marker in inflammatory bowel disease. Dig Liver Dis. 2009; 41:56-66) estimated that the lactoferrin test identified patients with IBD with a mean sensitivity of 80% and specificity of 82% while certain studies (von Roon A C, Karamountzos L, Purkayastha S, Reese G E, Darzi A W, Teare J P, Paraskeva P, Tekkis P P. Diagnostic precision of fecal calprotectin for inflammatory bowel disease and colorectal malignancy. Am J Gastroenterol. 2007; 102:803-13. [PubMed: 17324124]; Labaere, Delphine, et al. "Comparison of six different calprotectin assays for the assessment of inflammatory bowel disease." United European gastroenterology journal 2.1 (2014): 30-37) employing a calprotectin threshold concentration of 100 µg/g demonstrated sensitivity and specificity values of 98% and 96% respectively and studies employing a calprotectin threshold concentration of 50 µg/g demonstrated a sensitivity and specificity value of 89% and 81% respectively. In fact it has been shown that calprotectin screening may reduce the need for endoscopic procedures in adults with suspected IBD by as much as 67% (Van Rheenen, Patrick F., Els Van de Vijver, and Vaclav Fidler. "Faecal calprotectin for screening of patients with suspected inflammatory bowel disease: diagnostic meta-analysis." Bmj 341 (2010): c3369).

Furthermore, S100A12—another member of the S100 family of calcium binding proteins as calprotectin, at fecal levels greater than 10 mg/kg identified IBD with a sensitivity and specificity of 96% and 92% respectively in children (de Jong N S, Leach S T, Day A S. Fecal S100A12: a novel noninvasive marker in children with Crohn's disease. Inflamm Bowel Dis. 2006; 12:566-72. [PubMed: 16804393]; Sidler, Marc A., Steven T. Leach, and Andrew S. Day. "Fecal S100A12 and fecal calprotectin as noninvasive markers for inflammatory bowel disease in children." Inflammatory bowel diseases 14.3 (2008): 359-366) whereas in adults (Kaiser T, Langhorst J, Wittkowski H, Becker K, Friedrich A W, Rueffer A, Dobos G J, Roth J, Foell D. Faecal S100A12 as a non-invasive marker distinguishing inflammatory bowel disease from irritable bowel syndrome. Gut. 2007; 56:1706-13. [PubMed: 17675327]; Manolakis A C, Kapsoritakis A N, Georgoulias P, Tzavara C, Valotassiou V, Kapsoritaki A, Potamianos S P. Moderate performance of serum S100A12, in distinguishing inflammatory bowel disease from irritable bowel syndrome. BMC Gastroenterol. 2010; 10:118. [PubMed: 20946669]) S100A12 distinguished patients with IBD from those with irritable bowel syndrome by sensitivity and specificity of 86% and 96% respectively. It is noteworthy that S100A12 levels are also elevated in serum of IBD patients, serum tests do not distinguish IBD from irritable bowel syndrome with the same level of sensitivity and specificity as fecal assays.

Fecal biomarkers have been studied both as a diagnostic tool and a tool for monitoring response to therapy. The utility pertaining to monitoring response is especially valuable as it can predict disease relapse, announce a flare and thus advise clinicians on instigating treatment earlier or further testing.

An excreta disposal unit 100, for example a toilet or a water closet, is shown in cross-sectional diagram of FIG. 1, and includes a flushing mechanism 101, a water tank 102, a toilet seat 103, a toilet bowl 104, and which disposes of excreta via a path of travel 105.

BRIEF SUMMARY OF THE INVENTION

In some embodiments, analysis of excreta is performed in situ with a excreta disposal unit to detect the presence of biomarkers, and to provide information on disease, a state of well-being, and/or on nutrition.

In some embodiments, a system for analyzing excreta is configured to collect at least a portion of an excreta, and further configured to analyze the at least a portion of the excreta, wherein at least a portion of the system for analyzing excreta is configured to be embedded in an excreta disposal unit, and wherein the system for analyzing excreta comprises at least one electronic device.

In some embodiments, the at least one electronic device is a microprocessor configured to control at least a portion of the system.

In some embodiments, the system comprise s first unit configured to be embedded in an excreta disposal unit, wherein the first unit is configured to collect the at least a portion of the excreta, and a second unit configured to analyze the at least a portion of the excreta collected by the first unit.

In some embodiments, the first and second units are different units.

In some embodiments, the system is configured to homogenize the at least a portion of the excreta prior to the analysis by the second unit.

In some embodiments, homogenization includes centrifugation.

In some embodiments, the system is configured to analyze excreta from multiple users and associate results with each of the multiple users.

In some embodiments, analytes from the multiple users are detected and/or quantified per user in less than or equal to 360 minutes.

In some embodiments, the system is configured to detect analyte concentration ranging from 0.1 ng/ml to 100,000 µg/ml.

In some embodiments, the system is configured to self-sanitize.

In some embodiments, the second unit is configured to be in physical contact with the excreta disposal unit.

In some embodiments, the second unit is configured to be remotely located from the excreta disposal unit.

In some embodiments, the excreta disposal unit is a toilet.

In some embodiments, the at least a portion of the excreta is solid.

In some embodiments, the at least a portion of the excreta is liquid.

In some embodiments, the at least a portion of the excreta is feces.

In some embodiments, the at least a portion of the excreta is urine.

In some embodiments, the at least a portion of the excreta is serologic material.

In some embodiments, the first unit is configured to agitate the at least a portion of the excreta.

In some embodiments, the first unit comprises one or more transducers.

In some embodiments, the first unit comprises one or more microfluidic devices.

In some embodiments, the first unit comprises one or more mechanical pumps.

In some embodiments, the first unit comprises one or more optical devices.

In some embodiments, the one or more optical devices are configured to perform spectroscopic analysis within the first unit.

In some embodiments, the second unit comprises one or more microfluidic devices.

In some embodiments, the second unit comprises one or more mechanical pumps.

In some embodiments, the second unit comprises one or more optical devices.

In some embodiments, the one or more optical devices are configured to perform spectroscopic analysis within the second unit.

In some embodiments, the one or more optical devices comprises at least one electromagnetic radiation source.

In some embodiments, the one or more optical devices comprises at least one isotopic radiation source.

In some embodiments, the one or more optical devices comprises one or more photodetectors.

In some embodiments, the one or more optical devices comprises one or more photomultipliers.

In some embodiments, the second unit comprises an electronic device.

In some embodiments, the electronic device comprises one or more microprocessors.

In some embodiments, the electronic device comprises one or more transceivers.

In some embodiments, the electronic device comprises one or more transmitters.

In some embodiments, the electronic device comprises one or more receivers.

In some embodiments, the second unit comprises an electrical apparatus.

In some embodiments, the electrical apparatus comprises one or more batteries.

In some embodiments, the electrical apparatus comprises one or more power supplies.

In some embodiments, the second unit comprises a mechanical apparatus.

In some embodiments, the mechanical apparatus comprises one or more chambers configured to, during at least of portion of operation of the one or more chambers, rotate at greater than 10 rpm.

In some embodiments, the second unit comprises one or more heating elements.

In some embodiments, the mechanical apparatus comprises one or more sources of thermally cross-linkable fluids.

In some embodiments, the mechanical apparatus comprises one or more actuated valves.

In some embodiments, the first unit performs spectroscopy on the at least a portion of an excreta.

In some embodiments, the spectroscopy utilizes electromagnetic radiation of wavelength between 180 nm and 4 µm.

In some embodiments, the first unit and second unit are tethered.

In some embodiments, the system is configured to communicate with external electronic media and/or devices.

In some embodiments, the system is configured to utilize variations in electrical impedance to analyze the at least a portion of the excreta.

In some embodiments, the system is configured to utilize immunochromatography is to analyze of the at least a portion of the excreta.

In some embodiments, the system is configured to utilize enzyme-linked immunosorbent assays to analyze the at least a portion of the excreta.

In some embodiments, the system is configured to utilize enzyme-linked immunosorbent assays utilizing monoclonal antibodies.

In some embodiments, the system is configured to utilize enzyme-linked immunosorbent assays utilizing single chain domain antibodies.

In some embodiments, the system is configured to utilize immuno-particle analysis to analyze the at least a portion of the excreta.

In some embodiments, the immuno-particle analysis particle size range is 5 nm to 1000 µm.

In some embodiments, the first and second units are configured to be independently activated.

In some embodiments, the first and second units are configured to be collectively activated.

In some embodiments, at least one of the first and second units are configured to be autonomously activated.

In some embodiments, the autonomous activation occurs at least partially in response to a signal from at least one sensor.

In some embodiments, the at least one sensor comprises a biometric sensor.

In some embodiments, at least one of the first and second units are configured to be manually activated.

In some embodiments, an analysis system for analyzing excreta comprises a first portion of the analysis system, wherein the first portion is configured to be connected to an excreta disposal unit and configured to collect at least a portion of an excreta, and a second portion of the analysis system, wherein the second portion is configured to homogenize the at least a portion of the excreta collected by the first portion.

In some embodiments, the first and second portions of the analysis system are different.

In some embodiments, the homogenization includes centrifugation.

In some embodiments, a resultant supernatant of the centrifugation is analyzed by the analysis system.

In some embodiments, an analysis system for analyzing excreta comprises a first portion of the analysis system, wherein the first portion is configured to be connected to an excreta disposal unit and configured to collect at least a portion of an excreta, and wherein the analysis system is configured to detect analyte from multiple users.

In some embodiments, the analytes from the multiple users are detected and/or quantified per user in less than or equal to 360 minutes.

In some embodiments, the analysis system is configured to self-sanitize.

In some embodiments, the self-sanitation comprises at least a partially autonomous process.

In some embodiments, the self-sanitation comprises a fully autonomous process.

In some embodiments, the self-sanitation comprises at least one of using liquids of various pH, elevated temperatures, detergents, and thermally cross-linkable fluids.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention may be obtained, a more particular description of the invention briefly described above will be rendered by reference to specific embodiments thereof which are illustrated in the appended drawings. For better understanding, the like elements have been designated by like reference numbers throughout the various accompanying figures. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
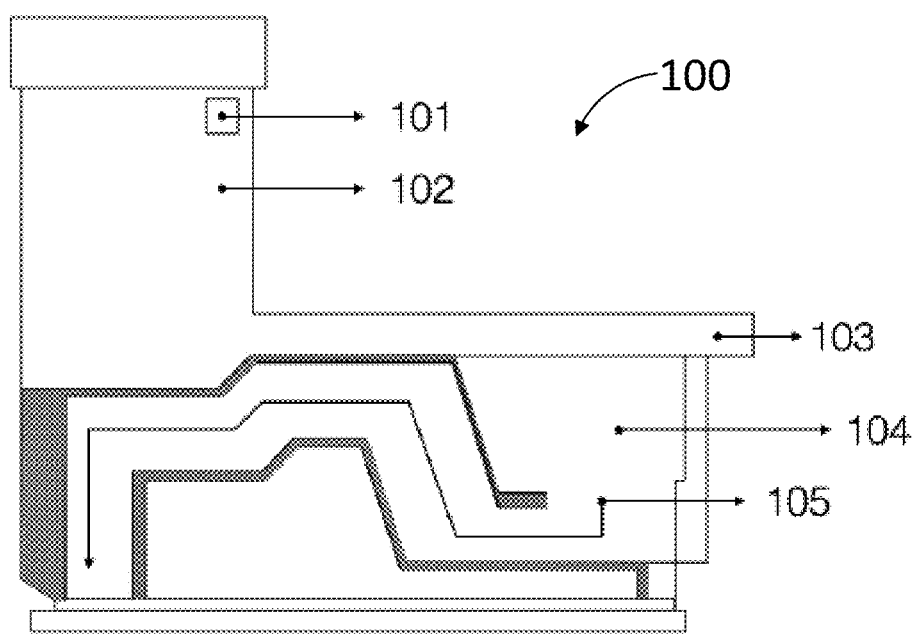
FIG. 1 is an illustration of a cross-sectional view of an excreta disposal unit, according to one embodiment.

Reference now will be made in detail to the presently preferred embodiments of the invention. Such embodiments are provided by way of explanation of the invention, which is not intended to be limited thereto. In fact, those of ordinary skill in the art can appreciate upon reading the present specification and viewing the present drawings that various modifications and variations can be made.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. Numerous embodiments are described in this patent application, and are presented for illustrative purposes only. The described embodiments are not intended to be limiting in any sense. The invention is widely applicable to numerous embodiments, as is readily apparent from the disclosure herein. Those skilled in the art will recognize that the present invention can be practiced with various modifications and alterations. Although particular features of the present invention can be described with reference to one or more particular embodiments or figures, it should be understood that such features are not limited to usage in the one or more particular embodiments or figures with reference to which they are described.

As such, those skilled in the art will appreciate that the conception, upon which this disclosure is based, can readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described process can be altered so that certain processes are conducted in parallel or independent, with other processes, to the extent that the processes are not dependent upon each other. Thus, the specific order of steps described herein is not to be considered implying a specific sequence of steps to perform the process. Other alterations or modifications of the above processes are also contemplated. For example, further insubstantial approximations of the apparatus, process and/or algorithms are also considered within the scope of the processes described herein.

In addition, features illustrated or described as part of one embodiment can be used on other embodiments to yield a still further embodiment. Additionally, certain features can be interchanged with similar devices or features not mentioned yet which perform the same or similar functions. It is therefore intended that such modifications and variations are included within the totality of the present invention.

In an embodiment, a system for analyzing excreta, wherein the system is configured to collect and analyze at least a portion of an excreta, wherein at least a portion of the system is configured to be embedded in an excreta disposal unit, and wherein the system comprises at least one electronic device.

In a further embodiment, an analysis system for analyzing excreta, comprises a first portion configured to be connected to an excreta disposal unit and configured to collect at least a portion of an excreta, and a second portion configured to homogenize the at least a portion of the excreta collected by the first portion.

In a further embodiment, an analysis system for analyzing excreta comprises a first portion of configured to be connected to an excreta disposal unit and configured to collect at least a portion of an excreta, and wherein the analysis system is configured to detect analyte from multiple users.

In accordance to some embodiments, an EEAD comprises one or more components configured to collect and analyze at least portion of an excreta, from one or more individuals. In some embodiments, at least a portion of the excreta is solid. In some embodiments, at least a portion of the excreta is liquid. In some embodiments, wherein the at least a portion of the excreta is feces. In some embodiments, wherein the at least a portion of the excreta is urine. In some embodiments, at least a portion of the excreta is serologic material.

Figure 2:
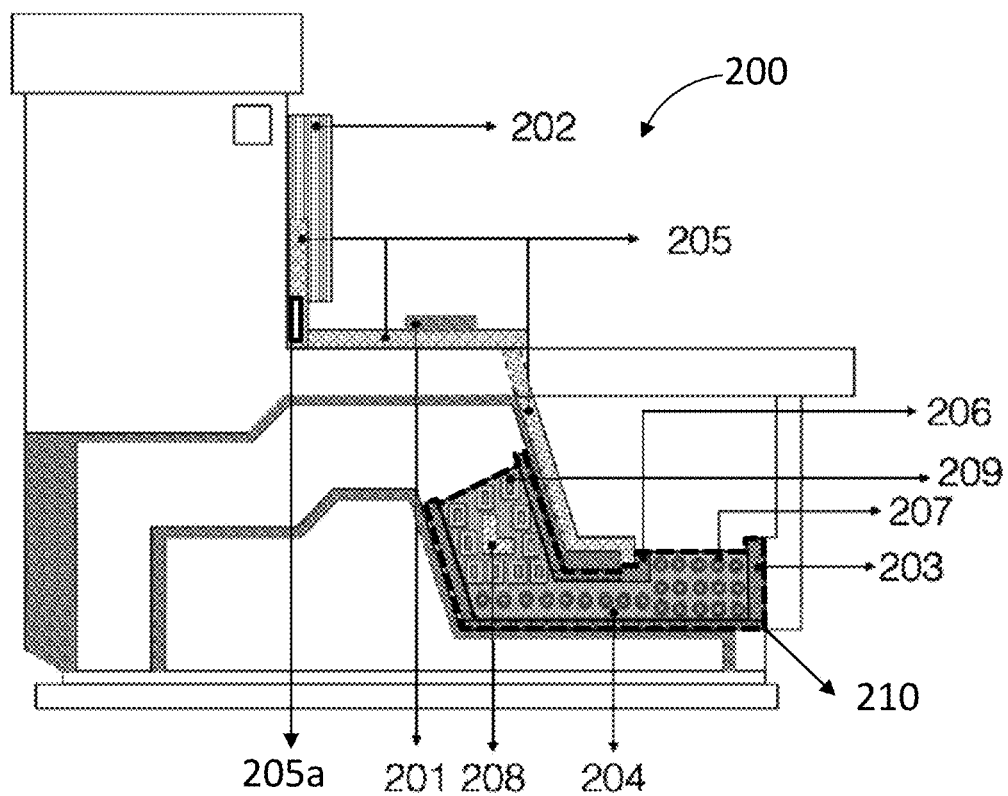
FIG. 2 is an illustration of a cross-sectional view of an excreta disposal unit including an embedded excreta analysis device, according to one embodiment.

FIG. 2 is a cross-sectional view of an excreta disposal unit including an embedded excreta analysis device, in accordance with one embodiment.

As illustrated in FIG. 2, EEAD 200 may comprise one or more biometric sensors 201. The one or more biometric sensors may provide information that enables the association of an excretion session to unique individuals, for example as may be accomplished by one or more portions of the EEAD 200 and/or by a system located remotely (e.g., one or more servers). In some embodiments, the biometric sensor may utilize a plurality of physiological parameters including based on body weight and associated pressure, body mass indices, fingerprint, retina, and/or body temperature, so as to enable the association and registering of the unique identity of individuals (e.g., by the biometric device(s), by the EEAD, and/or by a server). In some embodiments, the one or more biometric sensors 201 inform a central intelligence and analysis unit (CIAU) of the initiation of an EEAD session.

EEAD 200 may comprise a central intelligence and analysis unit (CIAU) 202. In some embodiments, the CIAU 202 is configured to be in physical contact with the excreta disposal unit. In some embodiments, the CIAU 202 is configured to be remotely located from the excreta disposal unit. The CIAU 202 may be mechanically affixed to any surface, for example, water tanks, wall, or floors in proximity to the host excreta disposal unit.

CIAU 202 may comprise a spectroscopy unit comprising one or more sources of radiation, for example a light source providing one or more wavelengths between 180 nm and 900 nm and/or isotopic radiation, one or more spectrometers, one or more photodetectors, for example a photodiode, one or more photomultiplier tubes and corresponding waveguides, and optical components including mirrors, gratings and lenses.

In some embodiments, CIAU 202 may perform analysis of collected excreta with one or more techniques. CIAU 202 may utilize variations in electrical impedance, immunochromatography, enzyme-linked immunosorbent assays (e.g., enzyme-linked immunosorbent assays utilizing monoclonal antibodies, enzyme-linked immunosorbent assays utilizing single chain domain antibodies), and/or immuno-particle analysis (e.g., wherein the immuno-particle analysis particle size range is 5 nm to 1000 μm).

CIAU 202 may comprise one or more reservoirs including a plurality of immunocytochemistry reagents, for example florescence tagging reagents using chemical indicators which chelate group I & II as well as transition metals, such indicators as fura-2, indo-1, fluo-3 and fluo-4, calcium green-1 and/or genetically encoded indicators (GECI) including green florescence protein (GFP), its variants, for example, circularly permuted GFP, YFP and CFP, and its fused form, and/or immunogold tagging and/or the utility of immuno-particle tagging wherein the particle is of dimension ranging from 5 nm to 1000 μm, or other forms of epitope and/or enzymatic tagging including but not limited to monoclonal and/or single-chain domain antibodies.

CIAU 202 may comprise collection, tagging and/or analysis components that may in turn comprise a microfluidic and/or micro-electromechanical system (MEMS) microfluidic and/or piezoelectric apparatus. CIAU 202 may comprise storage units for sanitation and/or decontamination materials.

CIAU 202 may comprise one or more electro-mechanical and/or mechanical actuators (e.g., a series of electro-mechanical and/or mechanical actuators) which control the release of materials from above-described reservoir(s).

CIAU 202 may comprise an analyzer which may utilize one or a plurality of spectral techniques, including but not limited to, transmission or absorption spectroscopy, florescence spectroscopy and/or florescence cytometry and/or raman spectroscopy and/or light scattering spectroscopy to interrogate the nature and concentration of biological and/or non-biological species in the excreta.

CIAU 202 may comprise an electronic unit which may provide a microprocessor, on board data storage, and/or connectivity (e.g., internet and/or Bluetooth). CIAU 202 may comprise at least one electronic device, (e.g., one or more electronic devices), including one or more microprocessors controlling at least a portion of the EEAD 200 (e.g., components of the CIAU 202 and/or the embedded unit 210) and/or processing acquired data, communication devices (e.g., wireless and/or wired connectivity, transceiver(s), transmitter(s), receiver(s)), and analog and/or mixed signal electronic devices that provide the control signals for the components of the EEAD 200 (e.g., CIAU 202 and/or the embedded device 210).

CIAU 202 may comprise an electrical apparatus, such as one or more power supply units (e.g., which may comprise one or more batteries and/or capacitors and/or connections to a wall outlet).

EEAD 200 may comprise an embedded unit 210 that is embedded in the volume, body, and/or surroundings of the excreta disposal unit, for example, a toilet as shown in FIG. 2 where walls 203 and 204 respectively correspond to the outer and inner walls of the embedded unit 210. The CIAU 202 may be remotely located and connected to the embedded unit 210 or may be in physical contact with the embedded unit 210. The embedded unit 210 may be configured to achieve conformity within the volume, body, or surroundings of the hosting excreta disposal unit.

In some embodiments, embedded device 210 and CIAU 202 are tethered. For example, EEAD 200 may comprise a tether 205 which connects the CIAU 202 with the embedded unit 210. The tether 205 can host a variety of functional correspondence between the CIAU 202 and embedded unit 210 including the delivery of interrogating radiation to interrogatable materials and associated spectroscopic response to analyzing a spectrometer and/or photodetector, delivery of supply power to the embedded unit, communication link, circulation of interrogatable material from the embedded unit 210 to the CIAU 202, and may include a mechanical apparatus, such as one or more pumps and/or actuators (e.g., actuated valves) and/or other mechanical devices. The CIAU 202 may include a mechanical apparatus comprising one or more chambers configured to, during at least of portion of operation of the one or more chambers, rotate at greater than 10 rpm. The CIAU 202 may include a mechanical apparatus comprising one or more sources of thermally cross-linkable fluids.

The CIAU 202 may include one or more heating elements and/or one or more refrigeration elements (e.g., a thermoelectric device). The heating and/or refrigeration elements may be configured to attain a pre-determined temperatures (e.g., a set temperature, or set temperature ranges) within the CIAU 202 (e.g., within a portion of the CIAU 202, such as within detachable unit 202k).

Embedded unit 210 may comprise a sensing unit 206 that detects the process of introduction and/or introduction of excreta into the environment of the apparatus. The sensing unit 206 may utilize independently or in combination a variety of methods, for example including optical, acoustic, mechanical and/or electric sensing to determine the onset of excretion of bodily waste into the excreta disposal unit. In some embodiments, the sensing unit comprises an imaging unit (e.g., a camera). In response to a signal provided as a result of the detection by the sensing unit 206, the EEAD 200 may initiate, immediately or with intentional delay, the agitation of the chamber of the embedded unit 210.

Embedded unit 210 may comprise an agitation unit configured to agitate and/or loosen excreta. The agitation unit may comprise one or more transducer(s) 207 that are configured to generate acoustic waves, for example ultrasonic, surface acoustic, and/or infrasonic waves, and/or electric charge to disperse and/or solubilize excreta within the agitation unit or through a section or entirety of the travel path of excreta in the excreta disposal unit.

Embedded unit 210 may comprise a collection unit 208 where the solubilized excreta is collected and/or temporarily stored in a temporary storage unit for subsequent processing including tagging and/or transport to subsequent processing sites dispersed at various locations in through the entirety of the EEAD 200. The solubilized excreta may, on its own or with further constitution, form the basis of interrogatable material which, in some embodiments, may be introduced into local microfluidic devices (and/or remote) microfluidic devices 209, that may be located throughout the entirety or at least a portion of the EEAD 200 (e.g., in the embedded unit 210, in the CIAU 202, and/or in the tether 205). In some embodiments, the collection unit 208 and/or the entire embedded unit may prompt the CIAU 202 and/or the user of the commencement, the progress of, and the completion of the collection of interrogatable materials, including, for example, the utility of light emitting devices and/or acoustic device to indicate process stage.

CIAU 202 may independently, or in tandem with the embedded unit 201 (e.g., the collection unit 208), initiate circulation of interrogatable materials and tagging or cytochemistry of interrogatable materials through a plurality of immunocytochemistry techniques for example histochemical staining, and/or florescence tagging using chemical indicators which chelate group I & II as well as transition metals such indicators as fura-2, indo-1, fluo-3 and-4, calcium green-1 and/or genetically encoded indicators (GECI) including green florescence protein (GFP), its variants for example, circularly permuted GFP, YFP and CFP, and its fused form, and/or immunogold tagging and/or the utilitization of immuno-particle tagging wherein the particle is of dimension ranging from 5 nm to 1000 µm, or other forms of epitope and/or enzymatic tagging, including, but not limited to, monoclonal and/or single chain domain antibodies.

CIAU 202 may independently, or in tandem with the embedded unit 201 (e.g., collection unit 208), initiate the homogenization of interrogatable materials using pulverization, and/or filtration and/or centrifugation at centrifugal speeds greater than 10 rpm (e.g., ranging from 10 rpm to 100,000 rpm), wherein the centrifugation chambers may be located within the CIAU 202.

Embedded unit 210 may comprise an analyzer which may utilize one or a plurality of spectral techniques, including, but not limited to, transmission or absorption spectroscopy, florescence spectroscopy and/or florescence cytometry and/or raman spectroscopy and/or light scattering spectroscopy, to interrogate the nature and concentration of biological and/or non-biological species in the excreta. Embedded unit 210 may perform spectroscopy utilizing electromagnetic radiation of wavelength between 180 nm and 4 µm.

In some embodiment, at least a portion of EEAD 200 (e.g., embedded unit 210, CIAU 202, tether 205, etc.) may self-sanitize (e.g., a regular pre-determined intervals, after each use, etc.). Embedded unit 210 may comprise a decontamination unit which is configured to effectively decontaminate critical systems components. For example, embedded unit 210 may comprise a decontamination unit that utilizes sanitizing agents including hot liquids of various pH, detergents and/or thermally cross-linkable fluids. The embedded unit 210 may include auxiliary components including one or more optical devices (e.g., electromagnetic radiation source(s) such laser(s) and/or LEDs, isotopic radiation sources, photodetectors, photomultipliers) and/or waveguides and/or pumps, including, for example, piezoelectric, peristaltic, or other mechanical pumps to aid with circulation of interrogatable materials (e.g., collected excreta and resultant materials). The one or more optical devices of the embedded unit 210 may be configured to perform spectroscopic analysis on the excreta.

Alternatively, or additionally, CIAU 202 may be configured to conduct spectroscopic analysis on collected excreta. CIAU 202 may include auxiliary components including one or more optical devices (e.g., electromagnetic radiation source(s) such laser(s) and/or LEDs, isotopic radiation sources, photodetectors, photomultipliers) and/or waveguides and/or pumps, including, for example, piezoelectric, peristaltic, or other mechanical pumps to aid with circulation of interrogatable materials (e.g., collected excreta and resultant materials). The one or more optical devices of the CIAU 202 may be configured to perform spectroscopic analysis on the excreta.

CIAU 202 may display results on a local display and/or the CIAU 202 may provide connectivity by remote or direct protocol, for example, through wireless, Bluetooth or ethernet connection to external devices such as mobile devices, personal computers, or servers. The CIAU 202 may relay data and/or analysis results to external devices for subsequent processing.

In some embodiments, decontamination of the microfluidic devices and/or interrogatable materials circulation systems is achieved using a variety of techniques independently or combination including for example utility of on-board sterilization reagents including liquids of various pH values, ultrasonic purification and electric charge and/or thermally cross-linkable fluids.

In some embodiment, interrogatable material associated with multiple different biometric identities can be sequentially collected, processed, and reported notwithstanding interrogation period of spectroscopic analysis. Interrogatable material associated with a unique biometric identity can be collected and temporarily stored in different storage units and/or microfluidic units wherein each temporary unit can be biometrically tagged to a particular biometric identity.

In some embodiments, the embedded unit 210 comprises an imaging unit configured to image the excreta deposited in the disposal unit.

In some embodiments, the embedded unit 210 contracts and/or expands as necessary to conform to the geometry of the excreta disposal unit housing and/or with an active or passive or dormant state of operation.

In some embodiments of the operation of the EEAD, activation of parts, or the entire, EEAD system occurs at least partially in response to a detection signal provided by one or more biometric sensors 201, at the onset of use of the disposal unit.

In some embodiments, the CIAU 202 and the embedded unit 210 are configured to be independently activated. In some embodiments, the CIAU 202 and the embedded unit 210 are configured to be collectively activated. In some embodiments, the CIAU 202 and the embedded unit 210 are configured to be autonomously activated. In some embodiments, the autonomous activation of the CIAU 202 and the embedded unit 210 occurs at least partially in response to a signal from at least one sensor (e.g., biometric sensor 201). In some embodiments, the CIAU 202 and the embedded unit 210 are configured to be manually activated.

Sensing unit 206 may detect or senses the onset of the deposition of excreta. In response to the sensing unit 206 detecting the onset of the deposition of excreta, one or more transducer(s) 207 agitate the excreta in the disposal unit.

Figure 3:
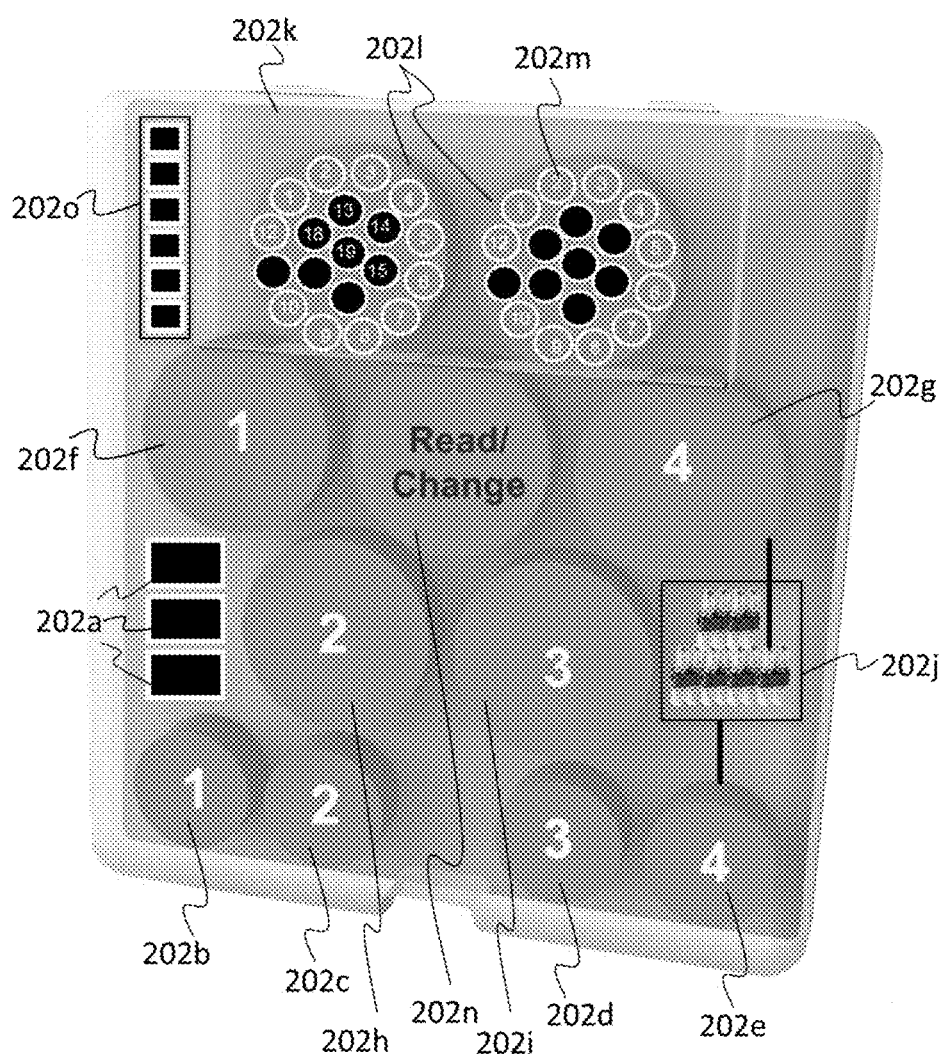
FIG. 3 is an illustration of internal components of a central intelligence and analysis unit, according to one embodiment.

CIAU 202 may then proceed to further process and analyze at least a portion of the excreta. To further describe the operation of the EEAD, FIG. 3 is provided as an illustration of internal components of CIAU 202, according to one embodiment.

CIAU 202 may comprise one or more pumps 202a that apply suction to the clean water reservoir unit 102 so as to transport clean water from the reservoir to the rest of the system, and/or to transport other fluids within the system, and/or to apply suction directly onto the embedded unit 210 so to transport the excreta from the embedded unit 210, through tether 205, and to chambers 202b, or 202c, or 202d or 202e. The chambers 202b-e may be horizontally rotating chambers assigned uniquely to each user.

Tether 205 may comprise of sieves and/or filters to discriminate and reject particles of a variety of dimensions, for example, tether 205 may comprise of a filter that rejects particles exceeding 50 µm. The posterior end (and/or anterior end) of tether 205 may comprise a homogenizer 205a, that may comprise a centrifugation system. In some embodiments, the homogenizer 205a, comprises a rotating blade that performs fine homogenization of collected excreta. Alternatively, or additionally, the homogenizer 205a may be part of the CIAU 202 and/or of the embedded unit 210.

Chambers 202*b-e* are configured to rotate at rotational speeds over 10 rpm to produce a supernatant. The supernatant may be transported (e.g., through tubing and/or channels, such as microfluidic channels) as a result of the operation of one or more pumps 202*a* from the chambers 202*b*, 202*c*, 202*d*, or 202*e* to the assay construction units 202*f*, 202*g*, 202*h*, or 202*i*, respectively.

Prior to transfer from chambers 202*b-e* to assay construction units 202*f-i*, the supernatant may be transferred into dilution network 202*j*. Dilution network 202*j*, which may comprise a series of valves, thermocouples, and/or tubing, may be employed to constitute the supernatant into different concentrations or to constitute other fluids in the system into different concentrations. The constituted fluids may then be incubated on a respective substrate in each respective assay construction unit 202*f-i*.

After incubation in the assay construction unit 202*f-i*, the substrate of the assay construction unit 202*f-i* is moved, such as by a mechanical device (e.g., using a three-axis head and/or a robotic arm) to an optical disc reader 202*n*. The optical disc reader 202*n* may be operated so as to acquire assay data, as described in U.S. Pat. No. 8,194,514, and incorporated by reference herein, in its entirety.

Acquired data may then be processed and/or transmitted by electronic unit 202*o*, which comprises at least one electronic device, (e.g., one or more electronic devices), including one or more microprocessors controlling at least a portion of the EEAD 200 (e.g., components of the CIAU 202 and/or the embedded unit 210) and/or processing acquired data, communication devices (e.g., wireless and/or wired connectivity, transceiver(s), transmitter(s), receiver(s)), and analog and/or mixed signal electronic devices that provide the control signals for the components of the EEAD 200 (e.g., CIAU 202 and/or the embedded unit 210). In some embodiments, the EEAD 200 (e.g., CIAU 202) is configured to communicate with external electronic media and/or devices (e.g., remote computing devices, such as one or more servers and/or one or more user devices).

Detachable unit 202*k* may be kept at refrigerated temperatures (i.e., less than room temperature, which may be required for the storage of some antibodies utilized by the CIAU 202) through the utility of thermoelectric units and/or other refrigeration units. Detachable unit 202*k* may comprise multiple sub-units 202*m* housed in housing 202*l*, which may in turn hold different fluids, such as fluids for bioassay (e.g., immunochemistry) analysis. Detachable unit 202*k* may also house one or more optical disc, that are utilized by optical disc reader 202*n*, as previously described, and which may be moved thereto by a mechanical device (e.g., using a three-axis head and/or a robotic arm).

Figure 4:
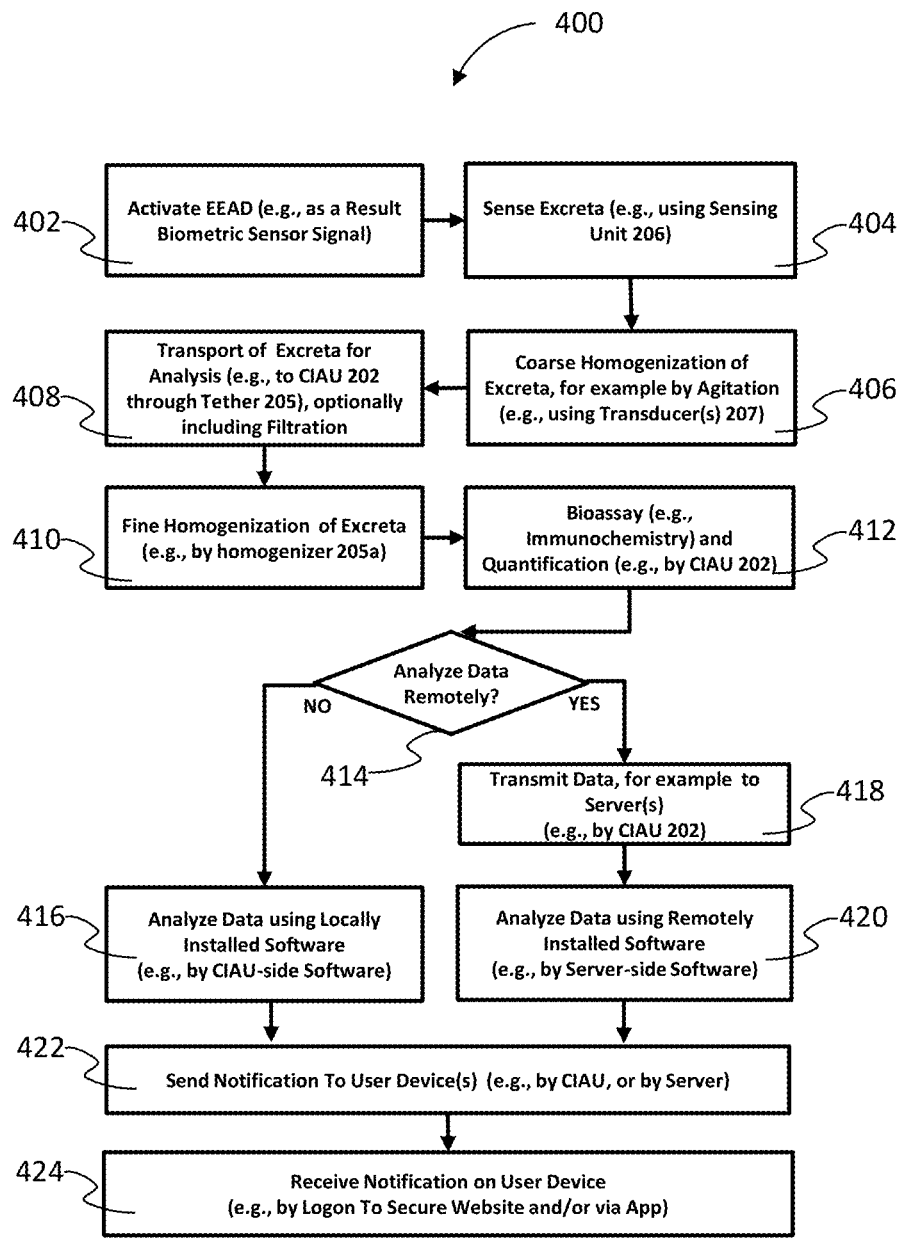
FIG. 4 is a flowchart illustrating the operation of a method for collection and analysis of excreta, according to one embodiment.

FIG. 4 is a flowchart illustrating the operation of a method 400 for collection and analysis of excreta, according to one embodiment. One or more acts of the method, or all of the method, may be performed by an EEAD, such as EEAD 200. One or more acts of the method may be performed by a server. One or more acts of the method may be performed by a user's device providing a user interface (e.g., computer, tablet, smartphone, smartwatch, smartspeaker, etc.).

The method 400 may include an act 402 wherein an EEAD 200 may activate as a result of a signal from a biometric sensor 201. Biometric sensor 201 may provide a signal to other portions of the EEAD 200 (e.g., embedded unit 210 and/or CIAU 202), which may activate the EEAD 200 so as to enable the commencement of collection and/or analysis of excreta. The signal provided by biometric sensor 201 may include information identifying the identity of the individual, as previously described. If identity of the user does not correspond to a user for whom analysis is authorized (e.g., household members), the EEAD can be configured to not activate and commence the collection and analysis of excreta. For instance, when visitors are using the excreta disposal unit, the EEAD may be configured to not activate.

The method 400 may include an act 404 of sensing of excreta, for example, using the sensing unit 206 of EEAD 200, as previously described. In response to the sensing act 404, the method 400 may include an act 406 of agitating the excreta, which accomplish coarse homogenization of the excreta. Act 406 may be performed by one or more transducers, such as the one or more transducers 207 of embedded unit 210 of EEAD 200.

The method 400 may include an act 408 of transport of excreta for analysis. The method may include filtration, for example through one or more sieves and/or filters disposed in the transport port. Act 408 may be performed by EEAD 200, and at least a portion of the coarse homogenized excreta may be transported via tether 205, which may include one or more filters (e.g., comprising filter media) that filtrate the excreta being transported.

The method 400 may include an act 410 of fine homogenization of the transported excreta. Act 410 may be performed by EEAD 200, for example, by homogenizer 205*a*, which may be located in the posterior (and/or anterior) end of tether 205, in CIAU 202, and/or in embedded unit 210.

The method 400 may include an act 412 of performing bioassay analysis, such as an immunochemistry analysis, of the homogenized excreta and quantifying of the results of the bioassay process, such as an immunochemistry process. Act 412 may be performed by CIAU 202, as previously described.

Upon quantification of the bioassay (e.g., immunochemistry) results data, the method 40 may include an act 414 of determining whether to conduct data analysis of the results data remotely (e.g., on one or more servers) or locally (on EEAD 200, such as on CIAU 202). Act 414 may be performed by the CIAU 202, and may involve accessing user settings that specify whether the user desires have data analysis conducted remotely or locally. Alternatively, CIAU 202 may be configured to only perform the data analysis of the results remotely. Alternatively, CIAU 202 may be configured to only perform the data analysis of the results locally. Alternatively, CIAU 202 may be configured to perform the data analysis both locally and remotely.

When data analysis is conducted locally, the method 400 may include an act 416 of analyzing the data using locally installed software, which may be performed by the CIAU 202 with software installed on the CIAU 202. Alternatively, or additionally, when data analysis is conducted remotely, method 400 may include an act 418 of transmitting bioassay (e.g., immunochemistry) data (and information identifying the user based on biometric data collected by the EEAD) to one or more remotely located computing devices, such as one or more servers, and corresponding receiving the data on the one or more remotely located computing devices, such as the one or more servers. Act 418 may be performed by CIAU 202 and data may be transmitted via wired and/or wireless communication methods and protocols. Method 400 may comprise an act 420 of analyzing the transmitted data using remotely installed software, which may be performed by the one or more remotely located computing devices, such as the one or more servers.

Method 400 may comprise an act 422 of sending a notification (e.g., pushing a notification) to one or more user device(s) corresponding to the user identified by the received information identifying the user. Act 422 may be performed by the CIAU 202 in the situation of local analysis, and/or act 422 may be performed by one or more remotely located computing devices, such as one or more servers, in the situation of remote analysis. The notification may include an indication to retrieve information and/or information itself, such as analysis results, recommendations for the user, user status results, user comparison to other population(s), and/or other relevant information.

Method 400 may comprise an act 424 of receiving the notification on one or more user devices. Act 424 may be performed by one or more user devices, such as one or more user computing devices, for example, computers, tablets, smartphones, smartwatches, and/or smartspeakers. Upon receiving the notification, the user may log onto a secure website and/or application to retrieve further information relevant to the user's status and analysis results, including both most recent information and/or historical information.

Figure 5:
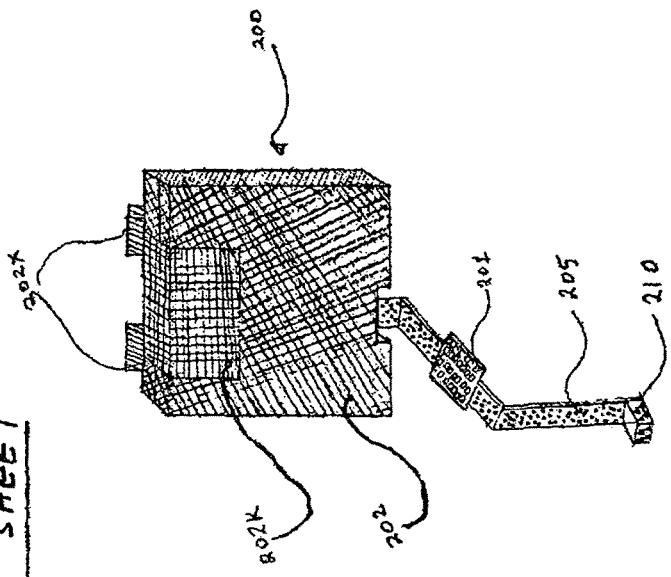
FIG. 5 is an illustration of an EEAD, according to one embodiment.

FIG. 5 is an illustration of EEAD 200, according to one embodiment. EEAD 200 may include one or more biometric sensors 201, an embedded unit 210, a CIAU 202, a tether 205, and a detachable unit 202k. EEAD 205 may include a housing for CIAU 202 that includes one or more attachment portions 202x that are configured to attach EEAD 205 (e.g., CIAU 202) to an excreta disposal unit. Attachment portions 202x may be hooks that hang over the edge of the water tank of the excreta disposal unit. The attachment points may be at one or more locations on the excreta disposal unit (e.g., toilet), for example a water tank of the excreta disposal unit, the top of the excreta disposal unit, and/or the seat of the excreta disposal unit.

Figure 6:
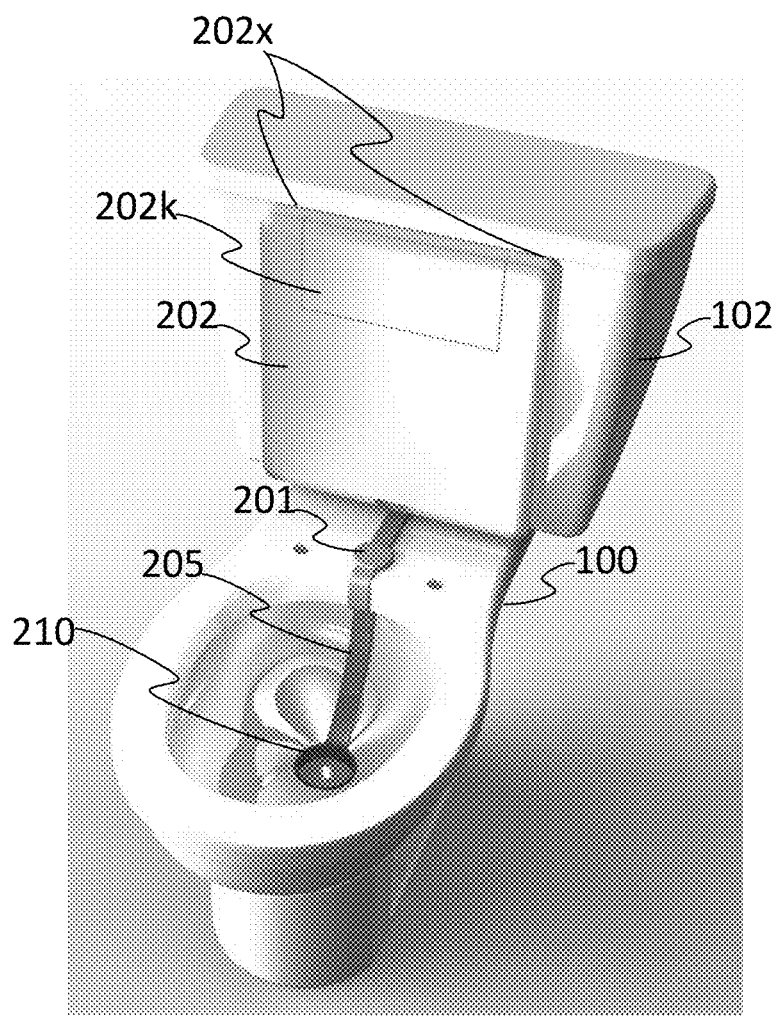
FIG. 6 is an illustration of an EEAD attached to a excreta disposal unit (e.g., toilet) via attachment portions, according to one embodiment.

FIG. 6 is an illustration of an EEAD 200 attached to a excreta disposal unit 100 (e.g., toilet) via attachment portions 202x on the water tank 102 of the excreta disposal unit 100.

Figure 7:
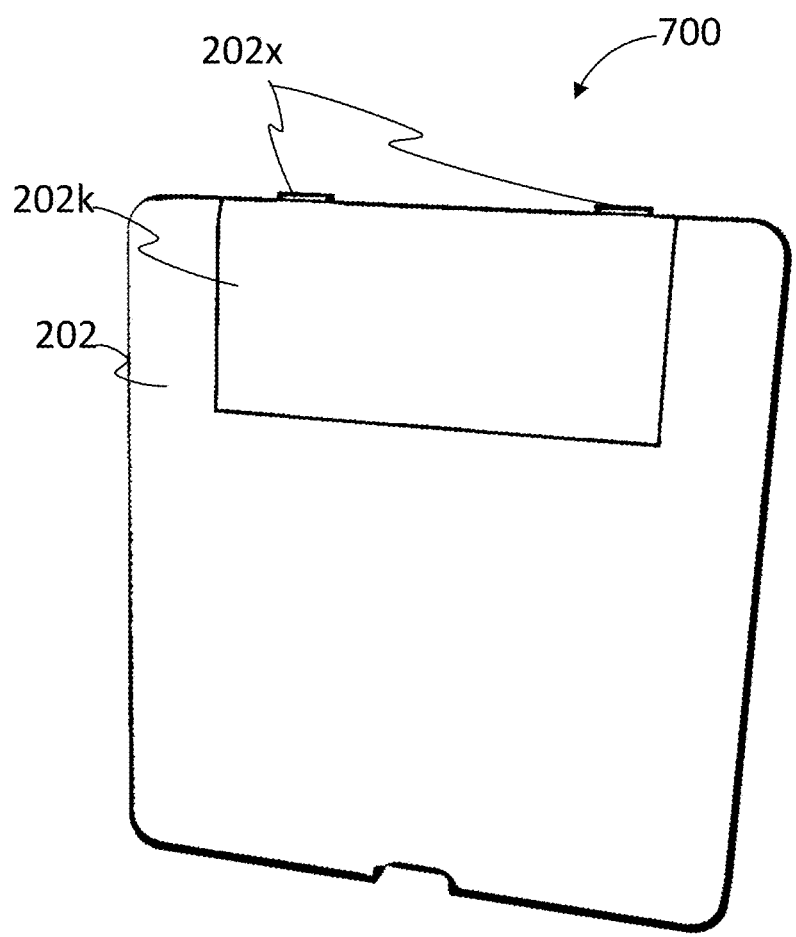
FIG. 7 is an illustration of an external housing front face of a CIAU, according to one embodiment.

FIG. 7 is an illustration of the external housing front face 700 of the CIAU 202.

Figure 8:
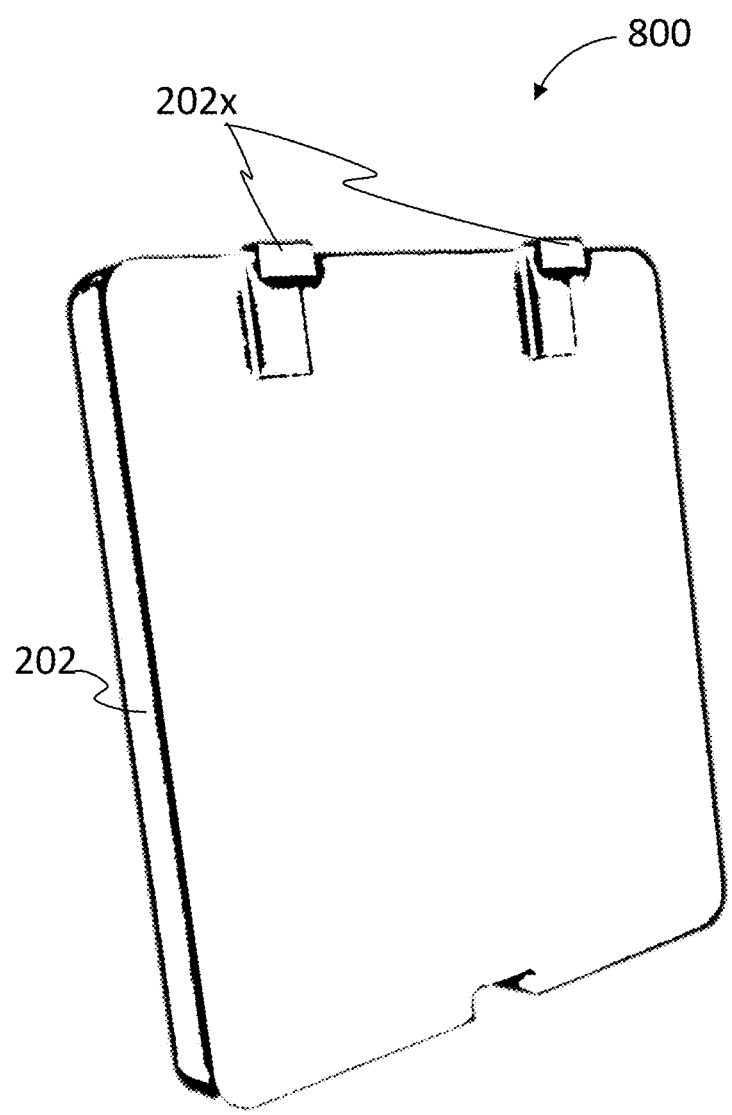
FIG. 8 is an illustration of an external housing back face of a CIAU 202, according to one embodiment.

FIG. 8 is an illustration of the external housing back face 800 of the CIAU 202, wherein the attachment portions 202x (e.g., attachment hooks) may be located at the back face 800 of the CIAU 202.

Figure 9:
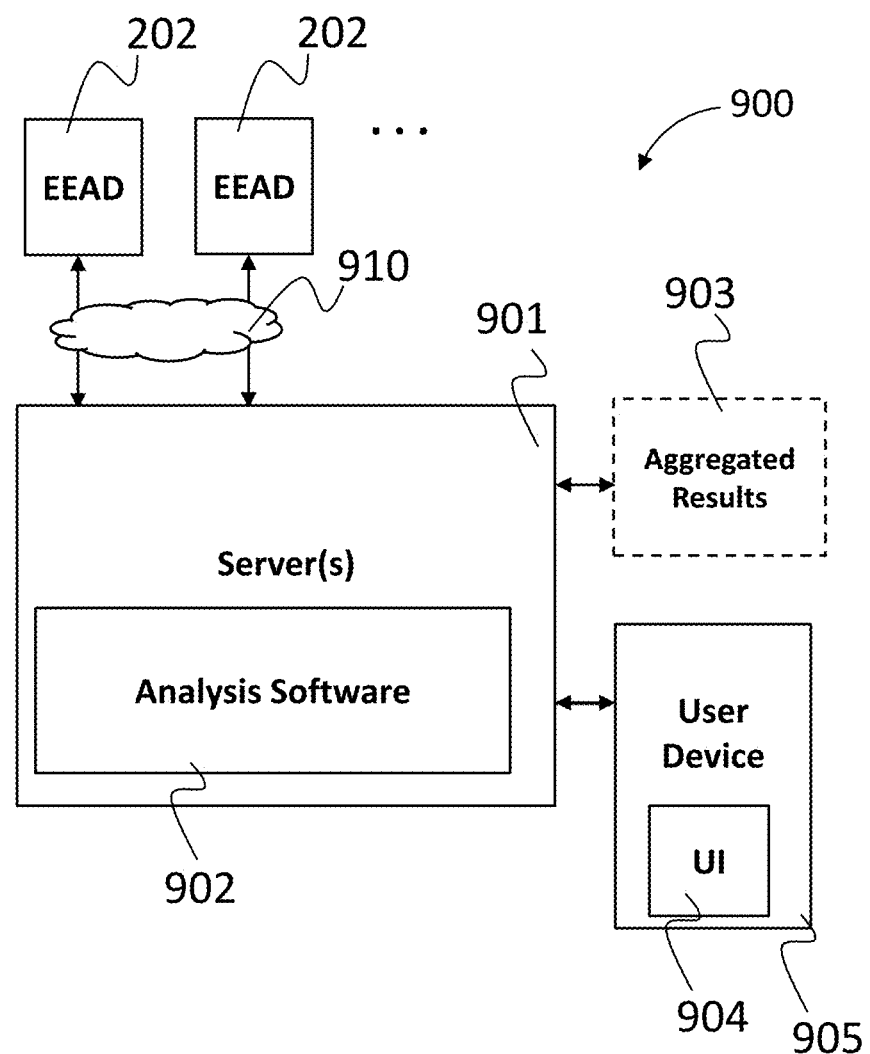
FIG. 9 is a schematic illustration of an excreta analysis system, according to one embodiment.

FIG. 9 is a schematic illustration of an excreta analysis system 900 including one or more EEAD(s), one or more servers 901, and/or one or more user devices 905. System 900 may enable communication between the one or more EEAD(s) 202, the one or more servers 901, and the one or more user devices 905.

In some embodiments, an excreta analysis system comprises one or more EEAD(s) 202 configured to connect via a network 910 and send (and/or receive) communication to one or more remote computing devices, such as one or more servers 901. The one or more servers 901 may comprise analysis software 902 installed on the one or more server 901. As described in relation to method 400, the one or more EEAD(s) 202 can transmit data relating to the quantified immunochemistry conducted by EEAD(s) (and information identifying the user based on biometric data collected by the EEAD), as described in act 418 of method 400. As described in act 420 of method 400, the one or more servers 901 can analyze the received immunochemistry data using installed server-side analysis software 902, and may send a notification to one or more user device(s) 905 corresponding to the corresponding identified user.

The one or more server(s) can communicate periodic software updates, data, and/or a variety of information to the EEAD(s) 202 and/or to the user device(s) 905, for example, by push notification to a smart-device, a handheld device, and/or an internet based account. The one or more server(s) 901 can format data associated with a plurality of users into aggregated results 903 and may present a variety of visualization, including for example, multi-dimensional (e.g., 2D, 3D) data visualizations of results from the plurality of users. The aggregated results 903 may be provided to one or more computing devices, for example to or more computing devices identified as being associated with authorized user(s) having authority to view aggregated results (e.g., based on user logon credentials). Alternatively, or additionally, the aggregated results 903 may be provided to the one or more user device(s) 905 corresponding to the corresponding identified user.

Figure 10:
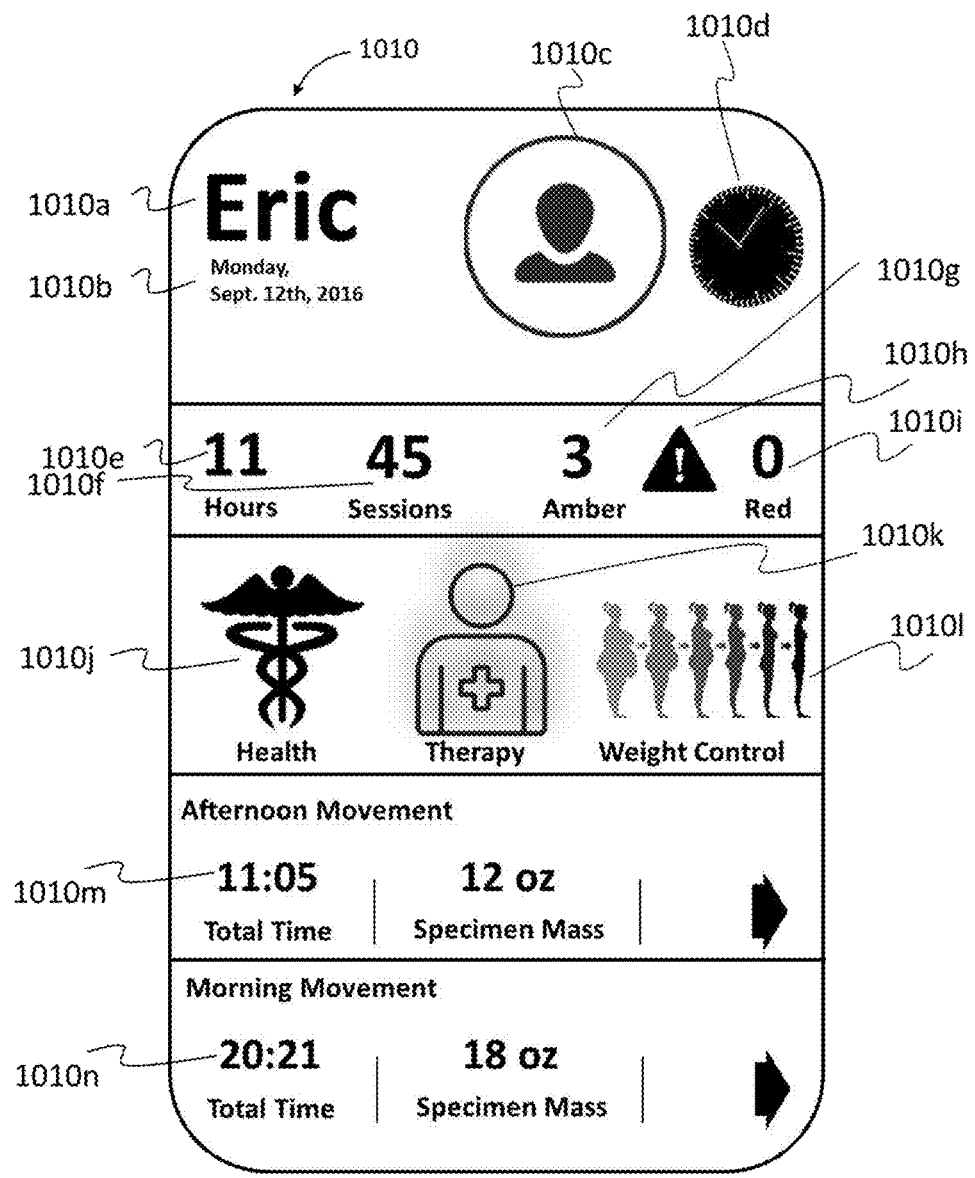
FIG. 10 is an illustration of a first user interface page, according to one embodiment.
Figure 11:
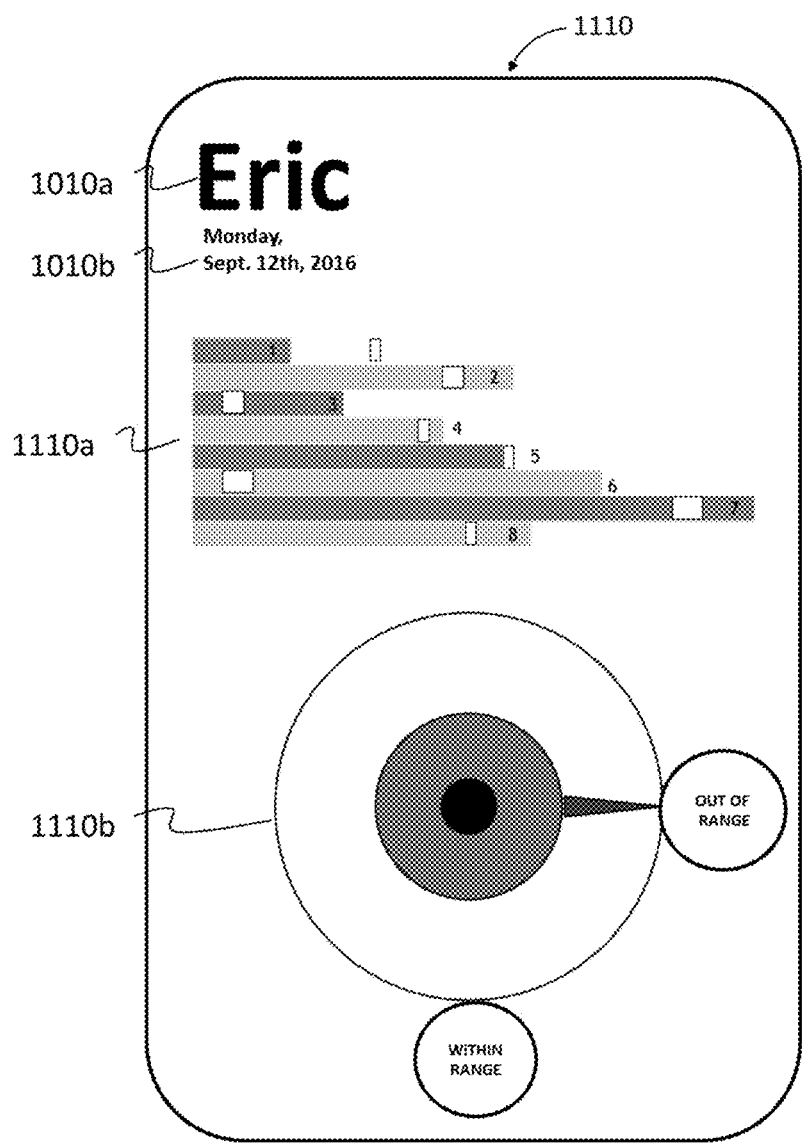
FIG. 11 is an illustration of a second user interface page, according to one embodiment.

The one or more servers 901 can communicate data and/or a variety of other information to the user by sending information to one or more user device(s) 905, which may in turn present the received information to the user via a user interface 904. User interface 904 may comprise of at least one page, page(s) 1010 and/or 1110, as shown in the illustrations of first and second user interface pages in FIG. 10 and FIG. 11, respectively.

First page 1010 of the user interface may comprise indication 1010a that provides the name of the user. Indication 1010b provides the date of the current session. Indication 1010c provides an image of the user (or any image selected by the user). Indication 1010d provides a display of current time.

Indication 1010e provides a count of the hours of use. Indication 1010f provides a count of the number of sessions. Indication 1010g (when displayed) provides a first alert type (e.g., referred to as an "amber alert") which indicates quantification of at least one biomarker in the user's excreta that has exceeded a designated first threshold, and may be a number corresponding to the number of biomarker in the user's excreta exceeding designated first thresholds. Indication 1010h (when displayed) provides a stationary or animated alert symbol for variety of information relayed to the user and can be of a variety of colors and/or formats. Indication 1010i (when displayed) provides a second alert type (e.g., "red alert") which indicates quantification of at least one biomarker in user's excreta that has exceeded a designated second threshold, and may be a number corresponding to the number of biomarker in the user's excreta exceeding designated second thresholds.

Indications 1010j, 1010k, and 10101 provide the user access to pages that have been designed to display organized information pertaining to the monitoring of overall and/or cumulative trends associated with a group of biomarkers that can indicate the progression of parameters associated with, for example, health, therapy, and weight control, respectively. For example, second page 1110 (FIG. 11) is the destination page the user arrives at upon activating indication 1010j. Indications 1010m and 1010n provide information pertaining to the most recently and second most recently quantified excreta, respectively, wherein a user selection of either indications 1010m or 1010n may provide the user with other pages comprising further information about the excreta quantification activity and results.

Second page 1110 may further comprise of indications 1010a and 1010b to identify the user, time, date and/or location. Indication 1110a provides a form of visualization of data associated with the organized information associated with the referenced segment, for example, health. Indication 1110b provides a summary visualization of the status of the information as above or below certain pre-determined range and guidelines. For example, layer 1110b provides the summary in the form of a dial indicator.

The terms "an embodiment", "embodiment", "embodiments", "the embodiment", "the embodiments", "an embodiment", "some embodiments", and "one embodiment" mean "one or more (but not all) embodiments of the present invention(s)" unless expressly specified otherwise.

The terms "including", "having," "comprising" and variations thereof mean "including but not limited to", unless expressly specified otherwise.

The term "consisting of" and variations thereof mean "including and limited to", unless expressly specified otherwise.

The enumerated listing of items does not imply that any or all of the items are mutually exclusive. The enumerated listing of items does not imply that any or all of the items are collectively exhaustive of anything, unless expressly specified otherwise. The enumerated listing of items does not imply that the items are ordered in any manner according to the order in which they are enumerated.

The terms "a", "an" and "the" mean "one or more", unless expressly specified otherwise.

Headings of sections provided in this patent application and the title of this patent application are for convenience only, and are not to be taken as limiting the disclosure in any way.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A system for analyzing excreta:
   wherein the system for analyzing excreta is configured to attach to a toilet and collect at least a portion of an excreta, and
   wherein the system for analyzing excreta is further configured to analyze the at least a portion of the excreta, and
   wherein at least a portion of the system for analyzing excreta is configured to be embedded in the toilet, and
   wherein the system for analyzing excreta comprises a plurality of rotating chambers assigned uniquely to each user and configured to produce a supernatant from the collected excreta, and
   wherein the system is configured to analyze excreta from multiple users and associate results with each of the multiple users.

2. The system of claim 1, further comprising an optical disc reader configured to acquire assay data from the supernatant incubated on a substrate.

3. The system of claim 2, comprising:
   a first unit configured to be embedded in the toilet, wherein the first unit is configured to collect the at least a portion of the excreta; and
   a second unit configured to analyze the at least a portion of the excreta collected by the first unit.

4. The system of claim 3, wherein the first and second units are different units.

5. The system of claim 3, wherein the system is configured to homogenize the at least a portion of the excreta prior to the analysis by the second unit.

6. The system of claim 2, wherein the substrate on which the supernatant is incubated comprises one or more optical discs configured to be utilized by the optical disc reader.

7. The system of claim 6, further comprising a detachable unit housing the one or more optical discs.

8. The system of claim 3, wherein the second unit is remotely located from the toilet.

9. The system of claim 3, wherein the first unit is configured to agitate the at least a portion of the excreta.

10. The system of claim 6, further comprising a mechanical device configured to move the one or more optical discs.

11. The system of claim 10, wherein the mechanical device is configured to move the one or more optical discs to the optical disc reader.

12. The system of claim 3, wherein the second unit comprises a dilution network to constitute the supernatant.

13. The system of claim 10, wherein the mechanical device comprises a three-axis head.

14. The system of claim 10, wherein the mechanical device comprises a robotic arm.

15. The system of claim 8, wherein the first unit and second unit are tethered, wherein the at least a portion of the excreta collected by the first unit is transported to the second unit.

16. The system of claim 3, wherein the system is configured to communicate with external electronic media and/or devices.

17. The system of claim 3, wherein the second unit comprises a plurality of reservoirs containing immunoparticles.

18. The system of claim 1, further comprising one or more transducers configured to generate acoustic waves that solubilize the collected excreta.

19. An analysis system for analyzing excreta, comprising:
   a first portion of the analysis system, wherein the first portion is configured to be connected to a toilet and configured to collect at least a portion of an excreta, and wherein the first portion comprises one or more transducers configured to generate acoustic waves that solubilize the collected excreta; and
   a second portion of the analysis system, wherein the second portion is configured to homogenize the at least a portion of the excreta collected and solubilized by the first portion.

20. An analysis system for analyzing excreta, comprising:
   a first portion of the analysis system, wherein the first portion is configured to be connected to a toilet and configured to collect at least a portion of an excreta;
   a second portion configured to produce a supernatant from the collected excreta; and
   an optical disc reader configured to acquire assay data from the supernatant incubated on a substrate, and
   wherein the analysis system is configured to detect a plurality of analytes for each user.

* * * * *